United States Patent
Yu et al.

(10) Patent No.: US 6,468,472 B1
(45) Date of Patent: Oct. 22, 2002

(54) CLEANING AND DECONTAMINATING DIALYZERS BY PER-COMPOUND SOLUTIONS

(75) Inventors: Zhi-Jian Yu, Irvine, CA (US); Stanley William Huth, Newport Beach, CA (US)

(73) Assignee: Metrex Research Corporation, Orange, CA (US)

( * ) Notice: Subject to any disclaimer, the term of this patent is extended or adjusted under 35 U.S.C. 154(b) by 0 days.

(21) Appl. No.: 09/397,543

(22) Filed: Sep. 16, 1999

(51) Int. Cl.[7] .............................. A61M 1/14; C11D 3/00; D06M 16/00; C23G 1/02; B08B 9/00
(52) U.S. Cl. .......................... 422/28; 422/48; 510/161; 510/367; 510/376; 435/264; 134/3; 134/22.13; 134/22.19; 134/36; 134/41
(58) Field of Search .................... 422/28, 44, 48; 510/161, 367, 376; 435/264; 134/3, 22.1, 36, 22.11, 41, 22.17, 22.19, 22.14, 22.13

(56) References Cited

U.S. PATENT DOCUMENTS

| | | | |
|---|---|---|---|
| 4,209,402 A | 6/1980 | Gentles | 210/137 |
| 4,332,264 A | 6/1982 | Gortz et al. | 134/57 |
| 4,444,596 A | 4/1984 | Gortz et al. | 134/18 |
| 4,444,597 A | 4/1984 | Gortz et al. | 134/18 |
| 4,690,772 A | 9/1987 | Tell et al. | 252/106 |
| 4,695,385 A | 9/1987 | Boag | 210/636 |
| 4,772,290 A | 9/1988 | Mitchell et al. | 8/107 |
| 5,173,125 A * | 12/1992 | Felding | 134/22.11 |

(List continued on next page.)

FOREIGN PATENT DOCUMENTS

| | | | | |
|---|---|---|---|---|
| EP | 0 873 687 A1 | 10/1998 | | A01N/37/16 |
| JP | 11-73680 | 3/1999 | | |
| WO | WO 96/40317 | 12/1996 | | |
| WO | WO 97/19594 | 6/1997 | | A01N/37/00 |
| WO | WO 97/40860 | 11/1997 | | |
| WO | WO 00/26334 | 5/2000 | | C11D/7/18 |

OTHER PUBLICATIONS

Martin et al., *APIC Guideline for Infection Preventoin and Control in Flexible Endoscopy*, Am J Infect Control, 22:19–38 (1994).

Rutala, William A., *APIC Guideline for Selection and Use of Disinfectants*, Am J Infect Control, vol. 24, 4:313–342 (1996).

Maisonneuve et al., *Cancer in patients on dialysis for end–stage renal disease: an international collaborative study*, The Lancet, vol. 354, pp. 93–99, Jul. (1999).

Kaplan et al., *Dialysate protein losses with bleach processed polysulphone dialyzers*, Kidney International, vol. 47, pp. 573–578 (1995).

Murthy et al., *Effect of Formaldehyde/Bleach Reprocessing on In Vivo Performances of High–Efficiency Cellulose and High–Flus Polysulfone Dialyzers*, J AM Soc Nephrol, 464–472 (1997).

Yuan et al., *Kinetics of Peracetic Acid Decomposition, Part I. Spontaneous Decomposition at Typical Pulp Bleaching Conditions*, The Canadian Journal of Chemical Engineering, vol. 75, pp. 37–41, Feb. (1997).

Primary Examiner—Robert J. Warden, Sr.
Assistant Examiner—Monzer R. Chorbaji
(74) Attorney, Agent, or Firm—Wood, Herron & Evans, LLP (57) ABSTRACT

A composition for cleaning and decontaminating medical devices such as dialyzers. A per-compound oxidant, for example, hydrogen peroxide ($H_2O_2$) and/or peracetic acid, is mixed with a buffer such as dipotassium hydrogen phosphate. The pH of the composition is between about 5–11. The composition effectively cleans the device, can achieve high level disinfection and sterilization of the device and is non-corrosive to plastics and adhesives used in the device.

29 Claims, 1 Drawing Sheet

U.S. PATENT DOCUMENTS

| | | | |
|---|---|---|---|
| 5,192,459 A | | 3/1993 | Tell et al. .................... 252/106 |
| 5,350,563 A | | 9/1994 | Kralovic et al. ............... 422/28 |
| 5,409,612 A | * | 4/1995 | Maltais et al. ............... 210/636 |
| 5,451,346 A | * | 9/1995 | Amou et al. ........... 252/186.23 |
| 5,480,565 A | * | 1/1996 | Levin et al. ................. 210/764 |
| 5,676,837 A | * | 10/1997 | Jungbauer et al. .......... 210/635 |
| 5,698,100 A | * | 12/1997 | Levin et al. ............. 210/321.6 |
| 5,827,542 A | | 10/1998 | Miner et al. ................ 424/616 |
| 5,840,343 A | * | 11/1998 | Hall, II et al. .............. 424/616 |
| 5,851,483 A | | 12/1998 | Nicolle et al. ................ 422/28 |
| 6,090,617 A | * | 7/2000 | Meserol ................... 435/285.2 |
| 6,096,348 A | * | 8/2000 | Miner et al. |
| 6,146,536 A | * | 11/2000 | Twardowski ................ 210/646 |
| 6,162,394 A | * | 12/2000 | Nicolle et al. ................ 422/28 |
| 6,165,318 A | * | 12/2000 | Paren et al. |

* cited by examiner

CLEANING AND DECONTAMINATING DIALYZERS BY PER-COMPOUND SOLUTIONS

FIELD OF THE INVENTION

The invention relates to chemical compositions and methods for using the compositions for cleaning and decontaminating dialyzers.

BACKGROUND

The medical industry and other industries utilize devices that are required to be cleaned and decontaminated. Cleaning is the removal of foreign material, including organic soil such as blood, feces, respiratory secretions, etc., from objects. It has been reported that failure to remove foreign material from a medical device such as an endoscope before a disinfection or sterilization process is likely to render the process ineffective. (Rutala, W A, APIC Guideline for Selection and Use of Disinfectants, Am J Infect Control, August 1996; Vol. 24,4:313–342). The presence of organic material or soil may contribute to the failure of disinfection by harboring embedded microbes and preventing the penetration of the germicide. Additionally, some disinfectants are inactivated by organic material (Martin, M A, Reichelderfer, M, APIC Guideline for Infection Prevention and Control in Flexible Endoscopy, Am J Infect Control, 1 994;22:19–38). Decontaminating is defined as the removal of hazardous or unwanted materials such as bacteria, mold spores or other pathogenic life forms and the like, with high-level disinfection and sterilization representing different levels of decontamination. High-level disinfection is a process that eliminates many or all pathogenic microorganisms, with the exception of bacterial spores, from inanimate objects. Sterilization is a process that completely eliminates or destroys all forms of microbial life, including fungal and bacterial spores.

High-level disinfection can be expected to destroy all microorganisms, with the exception of high numbers of bacterial spores. A Food and Drug Administration (FDA) regulatory requirement for high-level disinfectants is that they achieve 100% kill of 100,000 to 1,000,000 organisms of *Mycobacterium tuberculosis* in the presence of 2% horse serum in a quantitative tuberculocidal test. An additional FDA regulatory requirement for high-level disinfectants is that they must also achieve sterilization over a longer exposure time than the disinfection regimen time. Sterilization is tested with a sporicidal activity test utilizing spores of *Bacillus subtilis*.

Common commercially available high-level disinfectants include glutaraldehyde solutions between 2.4–3.4%, which typically require activation with an alkaline buffer just prior to use. Also available are an acidic (pH 1.6–2.0) 7.5%$^{w/v}$ hydrogen peroxide ($H_2O_2$) solution (Sporox®, Reckitt and Colman, Inc.) and an acidic (pH 1.87) mixture of 1.0% $H_2O_2$ plus 0.08% peracetic acid (PAA) (Peract™ 20, Minntech Corp. or CidexPA®, Johnson & Johnson). The minimum effective concentration of PAA for high-level disinfection at 25 minutes (min) and 20° C. is 0.05% (500 ppm) (Peract™). The minimum effective concentration of $H_2O_2$ for high-level disinfection at 30 min and 20° C. is 6.0% (Sporox®).

High-level disinfecting solutions are also typically designed for a reuse option, depending upon the medical device. For example, a glutaraldehyde high-level disinfecting solution for endoscope reprocessing may be reused for as long as 28–30 days, while kidney dialyzers are disinfected with single-use solutions.

Kidney dialyzers pose an additional problem in high level disinfecting in that the materials utilized require particular performance criteria of the cleaning and disinfection solutions. Types of dialyzers include: (1) coil, which incorporates a membrane in the form of a flattened tube wound around a central, rigid cylinder core, with a supporting mesh between adjacent portions of the membranes; (2) parallel plate, which incorporates a membrane in tubular or sheet form supported by plates in a sandwiched configuration; and (3) hollow-fiber, which incorporates the semipermeable membrane in the form of the walls of very small fibers having a microscopic channel running through them. Most parallel plate and hollow-fiber membranes are made from cellulose acetate, cellulose triacetate, regenerated cellulose, cuprophan or polysulfone.

The semipermeable membranes used in dialyzers have large areas and high porosities, and after use become coated with blood proteins and other organic and cellular material. Dialysis fibers are also often clotted with blood cells, proteins and other debris. As a result, the membrane of a used dialyzer has a reduced capacity for dialysis and is highly susceptible to microbial growth. Effective killing of microorganisms on such a used membrane for the purpose of reusing the dialyzer is difficult to accomplish without damaging the membrane.

When initially introduced, dialyzers were one-use devices. Since 1980, dialyzer reuse has risen dramatically in order to reduce the overall cost to the patient and the health care delivery system. Hemodialyzers, reprocessed in conformance with the Association for the Advancement of Medical Instrumentation (AAMI) specific guidelines and performance tests, have an average use number, that is, the number of times a particular hemodialyzer has been used in patient treatment. This number has been increasing over the years, from a United States average of 10 reuses in 1986 to 15 reuses in 1996. The cost benefits achieved by reprocessing are significant. For example, a new dialyzer costs about $20–30. With reprocessing, a dialyzer can be used between 5–20 times without substantial loss of efficacy. The cost of reprocessing is approximately $6.60–7.72 per unit, including reprocessing solutions. The cost per reuse for reprocessing solutions is $0.99–1.14 (average $1.08). The amortized dialyzer cost per reuse is $1.35–2.00, based upon an average reuse of 15 times. Additionally, the cost per reuse for dialyzer hazardous medical waste disposal is $0.50–0.55, reuse technician labor costs are $14/hr, and the associated labor cost of manual cleaning/dislodging clots is $0.23. Accordingly, with reprocessing, the dialyzer cost per treatment is conservatively less than about $10, as opposed to $30 if a new dialyzer were used for each treatment. A typical patient receives approximately 156 treatments per year. In 1998 in the United States alone there were approximately 280,000 patients on hemodialysis, and about 86% of hemodialysis centers have a dialyzer reuse program. Therefore, there are about 35,060,480 reuses in the United States (280,000×0.86×(156–156/15)). The U.S. market for reprocessing solutions in 1998 is estimated to be $34.7–40.0 million.

In addition to cost savings with dialyzer reuse, there are health advantages. Researchers have determined that reused dialyzers significantly mitigate patients' "new dialyzer" symptoms as well as immune reactions that often occur. The inherent clinical advantage of reused dialyzers has been attributed to both the reduction in trace contaminants such as ethylene oxide sterilant, and to the masking of immune reaction sites located on the membrane surface by protein deposits.

Dialyzer reprocessing involves three basic steps: (1) cleaning, (2) dialysis efficacy confirmation, and (3) high-level disinfecting involving soak times long enough to achieve sterilization. The cleaning step involves removing residual blood, organic and cellular material from the blood side and removing dialysate from the dialysate side of the semipermeable membrane. A number of cleaning solutions are known, including sodium hypochlorite bleach, PAA and $H_2O_2$. Purified water has also been used for cleaning. The cleaning solution must be rinsed from the dialyzer, typically with water.

Sodium hypochlorite bleach at a concentration of 0.5–1.0%$^{w/v}$ for 3 min exposure is utilized for cleaning. However, significant decreases in patient urea and creatinine clearance have been observed with high-flux polysulfone (F80B) dialyzers reprocessed with formaldehyde and bleach (Murthy et. al., Effect of Formaldehyde/Bleach Reprocessing on In Vivo Performances of High-Efficiency Cellulose and High-Flux Polysulfone Dialyzers. *J Am Soc Nephrol*:464472, 1997). Also, Kaplan and colleagues observed up to 20 g blood protein and specifically 15 g albumin loss into the dialysate per treatment with bleach-reprocessed, high-flux polysutfone (F80) dialyzers. Elimination of bleach from the reprocessing protocol led to a significant increase in serum albumin levels (Kaplan et al., Dialysate Protein Losses With Bleach Processed Polysulfone Dialyzers. *Kidney Int* 47;573–578, 1995). It is believed that reprocessing certain polysulfone dialyzers with bleach somehow alters membrane structure. Loss of the usual immune protection achieved with reused dialyzers has been shown to occur when sodium hypochlorite, particularly at elevated concentrations, is used for reprocessing, resulting in complement activation and neutropenia restored to near original levels. The problems associated with utilizing bleach in the reprocessing protocol have widespread ramifications; in the United States as of 1996, 42% of all patients were utilizing high-flux dialysis and 78% of those were utilizing polysulfone dialyzer membranes. Finally, while not reported within the kidney dialysis industry, it is known that chlorine bleach solution has a tendency to form so-called haloforms with organic compounds. These compounds are considered to be carcinogenic and are therefore also hazardous from the health perspective. In this context, it was recently reported that dialysis patients had an increase in cancer of 15% as compared to the general population (*The Lancet*, 354, 93–99, 1999).

Dialyzers reprocessed with prior art acidic $H_2O_2$ solutions have a significant reduction in ultrafiltration rate, indicating the presence of hydrolytically resistive protein deposits resistant to removal by $H_2O_2$. In addition, while prior art $H_2O_2$ solutions are useful in that they react vigorously with hemoglobin, can be effective in dissolving some clots in dialyzer headers and blood channels, and can restore dialyzer fiber bundle volume in some cases, elevated concentrations of $H_2O_2$ can rapidly generate gaseous oxygen reaction products, as evidenced by the reported bursting of noncompliant membrane capillary fibers. Acidic PAA reacts similarly with protein deposits, as PAA contains an equilibrium mixture of $H_2O_2$, PAA and acetic acid. Thus, acidic PAA will not remove protein deposits but can be effective in dissolving some clots.

Lastly, water used in the reprocessing cleaning step is generally ineffective in removing protein deposits or bound clots, as is the case with formaldehyde and glutaraldehyde.

The use of citric acid in connection with the cleaning of dialysis machines has been disclosed in a number of patents. Tell et al., U.S. Pat. No. 4,690,772, discloses a sterilizing and cleaning solution comprising sodium chlorite, citric acid and a sodium bicarbonate buffer. U.S. Pat. No. 5,480,565 to Levin discloses a method for reprocessing dialyzer cartridges used with kidney dialysis machines. The method involves filling the blood and dialysate compartments of the dialyzer with an aqueous solution containing citric acid at a concentration of about 1.0–5.0%$^{w/v}$ and then subjecting the dialyzer to an elevated temperature above 90° C. and below 100° C. for a period of at least 15 h. It is known, however, that citric acid is incapable of removing bound protein deposits from polymer surfaces at these temperatures. Moreover, the sodium chlorite solutions in the '772 patent have the capacity to crosslink proteins in surface deposits, making them even more resistant to removal. Also, the heat utilized in the '565 patent will further denature proteins and possibly create more deposits, as well as deposits which are more resistant to removal.

The efficacy confirmation step for dialyzer reprocessing involves confirming that membrane integrity and performance is substantially equivalent to that of a new dialyzer. Specifically, with respect to membrane performance, when the measured fiber bundle volume (FBV) of the membrane drops by 20%, the dialyzer is no longer reused.

The disinfection step involves subjecting the dialyzer to high level disinfection with a process or chemical disinfecting agent. Chemical disinfecting agents such as formaldehyde, glutaraldehyde or an acidic equilibrium mixture of PAA, $H_2O_2$ and acetic acid are typically employed. In the United States in 1996, 36% of dialysis centers used formaldehyde, 54% used PAA, 7% used glutaraldehyde and 3% used heat to disinfect and sterilize. A commonly used glutaraldehyde solution is Diacide® (Gulfstream Corp.), a 26%$^{w/v}$ concentrate of acidic glutaraldehyde which is activated with alkali just prior to use and then diluted with water to a final concentration of 0.8%$^{w/v}$. In 1998, the most commonly used PAA-based product was Renalin® Dialyzer Reprocessing Concentrate (Renal Systems Division, Minntech Corp.). Renalin® is a concentrated solution of acidic 4%$^{w/v}$ PAA and 24%$^{w/v}$ $H_2O_2$, designed to be diluted to a 3.5%$^{w/v}$ concentration in water, yielding a final concentration of about 0.14%$^{w/v}$ (1400 ppm) PAA and about 0.84%$^{w/v}$ (8400 ppm) $H_2O_2$. The minimum effective concentration of PAA to achieve either high level disinfection in a short time interval or sterilization over a longer soak period is 500 ppm.

Another PPA solution is described in Japanese patent JP 11076380A. An English translation of this patent discloses a cleaning and disinfecting composition consisting of an aqueous solution containing 3.5–6% hydrogen peroxide, 5–30% of an organic acid and 0.4–3.4% of an organic peracid in a weight ratio so that the sum of the acid and peracid to the peroxide is at least 1. The preferred organic acid is acetic acid. The method of cleaning and disinfecting comprises diluting the composition 20 to 100 fold with water. The composition may be used to clean the dialysis line of an artificial dialyzer through single step cleaning, allows easy removal of mass precipitation of calcium salts, and has high storage stability and high safety in handling. The Japanese patent does not explicitly reveal the solution pH; however, its reference to a solution having "high storage stability" (which Test 1 indicates is either four or eight weeks storage in darkness at 36° C.) would require a pH of substantially less than 5. It is thus essentially equivalent to other highly acidic PAA solutions such as Renalin®.

The chemical disinfecting agent must be able to be rinsed out of the dialyzer to below toxic levels, with a rinse-out period established for the particular agent. Typically, for glutaraldehyde disinfectants, 1 liter of isotonic sterile saline is perfused through the dialyzer fibers prior to dialyzer use, with sterile purified water additionally used to rinse the dialysate chamber. Moreover, since the dialyzer is connected to the vascular system during use, any residual chemical entity which may be reversibly bound to the semipermeable membrane and which may desorb from the dialyzer following the rinse should be non-immunogenic, i.e., it should not provoke an immune response.

While some of the above solutions enjoy some commercial success, all have inherent problems which limit their use. The alkaline glutaraldehyde solutions have an appreciable noxious odor and a low vapor threshold for toxicity, and thus require the concomitant use of a ventilation system. Glutaraldehyde also cross-links proteins and thus likely further clogs previously uncleaned dialyzers and further limits solute transport through the dialyzer fibers. The current commercial acidic $H_2O_2$ and PAA solutions do not efficiently clean dialyzers and result in limited dialyzer re-use life.

One potential solution to the aforementioned problems with highly acidic $H_2O_2$ and PAA solutions is the invention disclosed in U.S. Pat. No. 5,827,542. The '542 patent discloses a low odor, aqueous, quick acting, room temperature disinfecting and/or sterilizing solution that is non-corrosive to metals and elastomers used in medical instruments which are in need of sterilization and disinfection, having a pH within the range of from about 2.0 to about 6.0. The solution consists essentially of from about 1% to about 30% by weight of a peroxide and from about 1% to about 30% by weight of malonic acid, or salt form thereof, the solution being effective at room temperature to disinfect medical instruments within 30 min without corroding surfaces of the medical instruments. The '542 patent also discloses that the amount of peroxide component and the amount of malonic acid or carboxylic acid component are balanced such that the pH will be within the range of about pH 2.0–6.0, preferably about pH 3.0–5.0. However, all six patent examples at or above pH 5.0 do not achieve sterilization. Also disclosed is the composition packaging, wherein the composition may be prepackaged in solution form, ideally in two packages, one the peroxide and one the organic acid component, to be mixed at the point of use. This packaging is described as enhancing freshness. However, due to the slow approach to equilibrium between peroxide, organic acid and peracid, the production of the disinfecting peracid will not take place with the thirty min disinfection time specified by the patent. Thus, premixing of a peroxide and an organic acid component in the '542 patent is inoperative. Diluents such as alcohols can also be employed. While this invention discloses solutions with higher pH, up to pH 6.0, which are inherently much less corrosive to metals, it employs a high concentration of peracid generated from the combination of the peroxide and the malonic or other carboxylic acid. High peracid concentrations are known to be incompatible with medical device adhesives used to bond metal and plastic parts together. Solution compatibility tests with medical device adhesives were not disclosed, and claims for adhesive compatibility were also not made. An additional disadvantage of the '542 invention is the potential toxicity of the high concentrations of disclosed peracids, despite the unsupported statement to the contrary. The '542 invention did not disclose cleaning of medical devices such as kidney dialyzers.

Thus, it can be seen that there remains a need for a safe, practical, and efficient cleaning and high-level disinfecting and sterilizing composition and method for reprocessing kidney dialyzers.

SUMMARY OF THE INVENTION

The invention is directed to a composition for cleaning and decontaminating a dialyzer. The composition comprises a source of at least one per-compound oxidant and a buffer in amounts to provide the per-compound oxidant at a concentration and pH effective for cleaning and decontaminating the dialyzer. The composition has a pH between about 5–11. The per-compound oxidant may be at least one peracid or hydrogen peroxide ($H_2O_2$) and at least one peracid. In different embodiments, the $H_2O_2$ concentration may be in the range of about 1–50%$^{w/v}$, about 3–20%$^{w/v}$, or about 6.5–8%$^{w/v}$. The peracid may be at a concentration in the range of about 0.0050–10.0%$^{w/v}$. The per-compound oxidant may be a mixture of peracetic acid at about 0.0050–0.5%$^{w/v}$ and $H_2O_2$ at about 0.5–50.0%$^{w/v}$ or peracetic acid at about 0.005–0.2%$^{w/v}$ and $H_2O_2$ at about 0.5–8.0%$^{w/v}$. The buffer may be acetic acid, propanoic acid, glycine, monobasic dihydrogen phosphate, dibasic hydrogen phosphate, bicarbonate, and/or carbonate, either with or without non-immunogenic counter ions.

The invention is also directed to a method of cleaning and decontaminating a dialyzer. A solution is produced by combining at least one per-compound oxidant and a buffer, mixed prior to use, in amounts to provide the per-compound oxidant at a concentration and pH effective for cleaning and decontaminating the dialyzer. The dialyzer is contacted with the solution for a period of time effective for cleaning and decontaminating. The method may included a further step of removing the solution from the dialyzer, for example, by rinsing with sterile water or sterile saline. The dialyzer may be stored to prevent recontamination. A soiled dialyzer may be treated to remove soil before it is contacted with the solution, for example, by contact with an enzyme solution.

The invention is also directed to a method of cleaning and decontaminating a dialyzer having a blood chamber and a dialysate chamber. At least one per-compound oxidant and a buffer are combined in amounts and at a pH effective to form a cleaning and decontaminating solution, then the blood chamber is contacted with the solution for a time effective for cleaning and decontaminating. The solution may also contact the dialysate chamber. The dialyzer may be vented to allow escape of a gas formed from combining the per-compound and buffer.

These and other objects and advantages of the present invention shall be made apparent from the accompanying description and examples.

DETAILED DESCRIPTION

It has been discovered that a simple one-step mixing of a per-compound oxidant or per-compound oxidant mixture in a particular concentration range with a buffer to adjust the pH of the per-compound oxidant solution just prior to use results in a sufficiently stable solution which achieves simultaneous cleaning and high-level disinfection and sterilization of kidney dialyzers. Cleaning is defined herein as any significant restoration of dialyzer function such that its reuse life would be extended by at least one or more dialysis treatments. Cleaning efficacy can be measured by evaluating dialyzer membrane performance. The fiber bundle volume (FBV) of a hollow-fiber dialyzer is one measure of membrane performance as is membrane ultrafiltration rate. Mixing prior to use is achieved conventionally, for example, through hand or assisted mixing of two solutions in a suitable container. It is desirable to use readily mixed and soluble components so that the entire mixing operation lasts only a few seconds to not more than a few minutes in the case wherein one or more solid components is utilized. The present invention is particularly suited for the simultaneous cleaning and high-level disinfecting and sterilizing of artificial kidney dialyzers such as Polysulfone® dialyzers (Fresenius USA Corporation, Lexington, Mass.), but can also be used to clean other types of dialyzers including peritoneal dialyzers. In disclosing compounds and methods used to clean and decontaminate dialyzers, it is contemplated that the tubing or lines connecting to and from the dialyzer, for example, patient lines, are also encompassed by the invention.

The proper combination of per-compound, per-compound concentration and pH must be employed to achieve protein degradation and removal from a kidney dialyzer (e.g., cleaning) simultaneously with disinfection and sterilization. Generally, lower molecular weight per-compounds at higher concentrations and higher pH values are more efficacious. The term per-compound oxidant, as used herein, is any compound which delivers active oxygen in solution and which can achieve high-level disinfection and sterilization of kidney dialyzers. Thus, for example, peracetic acid (PAA) or other peracids, alone or in combination, which achieve high-level disinfection and sterilization are included in this definition.

In one embodiment, peracids produced from $C_1$–$C_4$ mono or dicarboxylic acids, such as performic acid, peracetic acid and perpropionic acids are used. Peracids produced from carboxylic acids with linear, saturated or unsaturated hydrocarbon chains having 5–20 carbon atoms such as linoleic acid ($C_{18}H_{32}O_2$) may also be used. Combinations of hydrogen peroxide ($H_2O_2$) or other peroxides with one or more peracids are also included. Solid sources of $H_2O_2$ such as sodium percarbonate and sodium perborate can be used in combination with one or more peracids or one or more solid peracid precursors, such as tetracetylethylenediamine (TAED) or acetylsalicylic acid. Generally, the concentration of peracid or peracid mixtures in the present invention ranges from about $0.0050\%^{w/v}$ to about $10\%^{w/v}$. In one embodiment combinations of PAA and $H_2O_2$, wherein the concentration of PAA is between about $0.0050\%^{w/v}$ and $0.5\%^{w/v}$ and the concentration of $H_2O_2$ is between about $0.5\%^{w/v}$ and $50.0\%$–, are used. In another embodiment, the concentration of PAA is between about $0.08\%^{w/v}$ and $0.2\%^{w/v}$ and the concentration of $H_2O_2$ is between about $0.5\%^{w/v}$ and $8.0\%^{w/v}$. Since peracids are generally unstable at higher pH and must be typically kept at a pH less than 3–4 to achieve shelf stability, they are kept separate from the buffer until just prior to use.

Peracid solutions are typically pH stabilized to between about pH 1–3 prior to mixing with the buffers of the invention. The peracid solutions are even more stable between about pH 1.6–2.0. This is achieved with an acidic compound such as an inorganic or organic acid. Organic acids with the greatest stabilizing effects are those which are precursors for the particular peracid(s) employed, e.g., acetic acid most efficiently stabilizes PAA. This is due to the well known equilibrium between $H_2O_2$, acetic acid and PAA. The amounts of each in a stable solution will be determined by the known equilibrium constant for the formation of PAA from $H_2O_2$ and acetic acid. Similar considerations apply to other peracids. Additionally, transition metals such as iron, manganese and copper also destabilize peroxides and peracids. Such metal-induced destabilization can be prevented with sequestrants such as hydroxy-ethylidene diphosphonic acid (Dequest 2010™ Monsanto Co.), or with the use of conventional chelating agents such as ethylenediamine tetraacetic acid (EDTA). Concentrations of Dequest 2010™ between about 0.10 and $1.0\%^{w/v}$ are used in one embodiment. Other conventional means of stabilizing peroxides and peracids can also be employed, such as the use of nitrilotrismethyl-, methyl- and other phosphonic acids.

A liquid or solid per-compound(s) may be utilized in the compositions and methods of the present invention. The solid per-compound(s) such as sodium perborate $SWHO_2y$ and a peracid precursor such as TAED would be mixed just prior to use with water and the buffer, or alternatively directly with a liquid buffer.

Generally, a pH between about 5–11 is useful in the present invention. The particular pH selected for a particular composition is dependent upon several testable factors, such as type, amount and stability of per-compound(s) and the particular kidney dialyzer application, e.g., type and amount of protein-containing deposit to be removed, rate of disinfection and/or sterilization required and device compatibility. The present invention generally destabilizes the per-compound due to the pH range employed. This destabilization is controlled for the particular application. Control of the destabilization of a particular per-compound is achieved through conventional studies of the particular equilibrium or equilibria involved in the formation and stabilization of the peracid as well as studies of decomposition rates versus pH and other solution parameters. For example, it is known that peracetic acid decomposition follows a second-order dependence on peracetic acid concentration with a maximum rate at pH 8.2 (Z. Yuan et al., *The Canadian Journal of Chemical Engineering*, Vol. 75, February, 1997, pp. 37–41). Buffers useful in the present invention will generally have pKa's of between about 4.5 and 11.5. The buffers must be compatible with the per-compound(s) with which they are paired in terms of buffer and per-compound short-term stability after mixing, e.g., about 48 hours or less for an application for reprocessing (cleaning and disinfecting or sterilizing) a used kidney dialyzer. The buffer also must maintain the desired pH during the use period. Buffer concentrations between about 2 mM and about 2 M can be used in compositions of the present invention. Buffers such as acetic acid (pKa=4.76), propanoic acid (pKa=4.86), glycine (pKa2=9.78), monobasic dihydrogen phosphate, dibasic hydrogen phosphate, bicarbonate or carbonate, each with a suitable counter ion such as sodium or potassium or another counter ion, can be used. Acetic acid can be used to buffer the solution to between pH 5.0–5.8. However, in a peracetic acid system, the amount of peracetic acid which can be stably maintained with an acetic acid buffer at pH 5.0–5.8 is less than 700 ppm. This is due to the shift in the equilibrium relationship between hydrogen peroxide, peracetic acid and acetic acid and the high rate of peracetic acid loss at higher pH. Non-immunogenic buffers and counter ions are generally used with kidney dialyzers. Potentially immunogenic buffers and counter ions can also be used with kidney dialyzers, as long as they can be completely rinsed from the dialyzer prior to use. A hydroxide buffer such as sodium or potassium hydroxide can also be used, alone or in combination with other buffers, in some circumstances. The buffer may be a liquid or solid.

The purity of the raw materials used in the compositions of the invention for kidney dialyzer use must be considered.

All per-compounds, peroxides and buffers should be of the highest possible purity, taking into account raw material costs, in light of the need to avoid provoking the immune system through exposure of trace amounts of undesirable chemicals should any contaminants in the raw materials desorb in trace amounts into the blood from a kidney dialyzer during dialysis. Moreover, compositions of the present invention need to be kept as simple as possible in terms of number of components for dialyzer reprocessing applications, to minimize and avoid immune response complications. Ideally, all components of the compositions of the present invention should be structurally similar, if not identical, to naturally occurring chemical entities found in the body so as to avoid immune responses from trace amounts which may inadvertently come into contact with the vascular system during dialysis.

In addition to the compositions of the invention not provoking an immune response in a patient, the compositions also should not be harmful to the patient in small amounts that may not be completely removed from the dialyzer. For example, a composition that contained anti-corrosive agents such as benzotriazole, chromates, dichromates, molybdates, vanadates, tungsdates, etc. would be harmful to patients. The compositions of the invention achieve cleaning and decontaminating of dialyzers without harm to patients.

Renalin®, the solution which upon dilution yields a final acidic (pH <2.5) concentration of $0.14\%^{w/v}$ PAA and $0.84\%^{w/v}$ $H_2O_2$, can also be utilized in combination with a suitable buffer to raise the pH to a level which effects cleaning of a kidney dialyzer without compromising disinfection and sterilization. Other peracid concentrates which are diluted with an aqueous buffer just prior to use can also be used. Peract™ 20 (Minntech Corp.) or Cidex PA® (Johnson and Johnson), which is the acidic (pH 1.87) mixture of $1.0\%^{w/v}$ $H_2O_2$ and $0.08\%^{w/v}$ PAA, can also be utilized in combination with a suitable buffer to raise the pH to a level which affects cleaning of a kidney dialyzer without compromising disinfection and sterilization.

The method of the invention for cleaning and decontaminating a kidney dialyzer generally involves the following steps: (1) combining a per-compound oxidant and a buffer in amounts effective for cleaning and decontaminating a kidney dialyzer, and (2) contacting the kidney dialyzer with the per-compound and buffer for a time sufficient to simultaneously clean and decontaminate the kidney dialyzer. The contacting time can be very short, for example 10 min or 48 hours or even longer, as long as the standards herein for cleaning and decontamination are achieved.

One embodiment of the present invention used for cleaning and decontaminating kidney dialyzers employs a gas-venting filter cap placed over at least one of the dialyzer fiber bundle (blood chamber or dialysate chamber) access ports to vent any oxygen gas produced from the per-compound and buffer solution. Per-compound solutions are generally stable at values below about pH 3–4. Higher pH values are known to destabilize per-compound solutions, with greater destabilization occurring with higher pH. This destabilization results in the production of oxygen gas. The amount of gas formation can be very high in some solutions, depending upon the type, concentration and pH of the per-compound solution. An example of this is the known production of 100 ml of oxygen from 10 ml of $3\%^{w/v}$ $H_2O_2$ when the latter is completely catalytically neutralized. The fiber bundle volume of a new dialyzer is approximately 100 ml and that of a used dialyzer is no less than 80% of the new volume. The result is that a considerable amount of oxygen gas can be potentially produced from a per-compound and buffer solution of the present invention. Thus, the method of the present invention for cleaning and decontaminating a kidney dialyzer generally involves the following steps: (1) combining a per-compound oxidant and a buffer in amounts effective for cleaning and decontaminating the dialyzer; (2) venting the dialyzer to allow increased gas to escape; and (3) contacting the dialyzer with the per-compound and buffer for a time sufficient to simultaneously clean and decontaminate the dialyzer. Alternatively, step (2) may be performed prior to step (1) or after step (3). More specifically, the inside of the empty dialyzer fiber bundle, and optionally the inside of the dialysate chamber, are filled with one of the solutions of the invention. One end of the dialyzer fiber bundle blood chamber is capped with a gas- and solution-impermeable cap, and the other end opening is capped with a gas-only venting cap, typically comprised of a hydrophobic barrier filter placed inside a regular cap with a physical hole or other gas channel or transport construction. Alternatively, both openings of the dialyzer fiber bundle blood chamber are capped with a gas-venting cap. Alternatively, any or all openings of both the blood and dialysate chamber are capped with a gas-venting cap. The hydrophobic barrier filter prevents water passage but allows gas passage through the gas channel on the opposite side of the barrier filter from the blood or dialysate chamber access port. The hydrophobic barrier filters and caps useful in the present invention are of conventional types and are commercially available from a variety of sources. An example of a suitable filter and cap is a Gore-Tex® membrane (W. L. Gore Associates, Inc., Elkton, Md.) and a polypropylene cap (Rexam Closures, Evansville, Ind.). The entire blood contact surface of the dialyzer is contacted with the solutions of the invention. Both ends of the fiber bundle should, in most cases, be covered with the solution, as a considerable amount of clotted blood and bound protein is typically found on used dialyzers at the ends of the fiber bundles.

The first step in the general method of the invention wherein the per-compound and buffer are combined can be preceded or followed by a step to remove soil from the dialyzer. This soil removal step can be comprised of contacting the dialyzer with an enzyme. Another embodiment of the method of the invention includes a step wherein the per-compound and buffer solution is removed from the dialyzer following the contacting step. This removal can be accomplished with a sterile water or saline rinse. Other sterile solutions such as dextrose or glucose solutions can also be used. The solution removal step can be followed by storage of the device in a way which prevents recontamination either by microorganisms or soils.

Other energy input may be employed to potentiate the solution's cleaning and decontaminating effects. For example, heat and ultrasonic energy are known to potentiate the speed at which chemical cleaning and disinfecting agents work. The practice of this invention is not to be limited by temperature except by those temperature extremes which would substantially inactivate the capability of the chemistry employed and/or damage the kidney dialyzer, as can be determined through routine performance and stability testing.

EXAMPLE 1

Cleaning and Disinfecting Efficacy at Various pH Values

Two used kidney dialyzers obtained from a dialysis clinic were used for testing the cleaning efficacy of $H_2O_2$ cleining and disinfecting solutions of the present invention at different pH values. The solutions in this example consisted of 7.5%$^{w/v}$ H$_2$O$_2$ at pH 4.0 and 8.5, the latter which was adjusted with NaOH. The fiber bundle volumes of the used dialyzers were measured as follows: after both blood chamber and dialysate chamber of a dialyzer were filled with tap water, the dialyzer was tapped repeatedly to rid the chambers of air bubbles and all four outlets/inlets of the dialyzer were plugged to prevent water loss. The dialyzer was weighed before and after the water in the blood chamber was evacuated. Evacuation was accomplished by blowing compressed air through the chamber. The blood chamber (fiber bundle) volume was determined as the difference between the two weight values divided by the density of water. The used dialyzer initial (before treatment with the cleaning/disinfecting solution) volumes ($V_{used}$), measured with the above method are consistent with the labeled minimum volumes (measured by the dialysis clinic) which are about 80% of the new dialyzer full volumes before the fiber bundles were clotted with patient blood.

Figure 1:
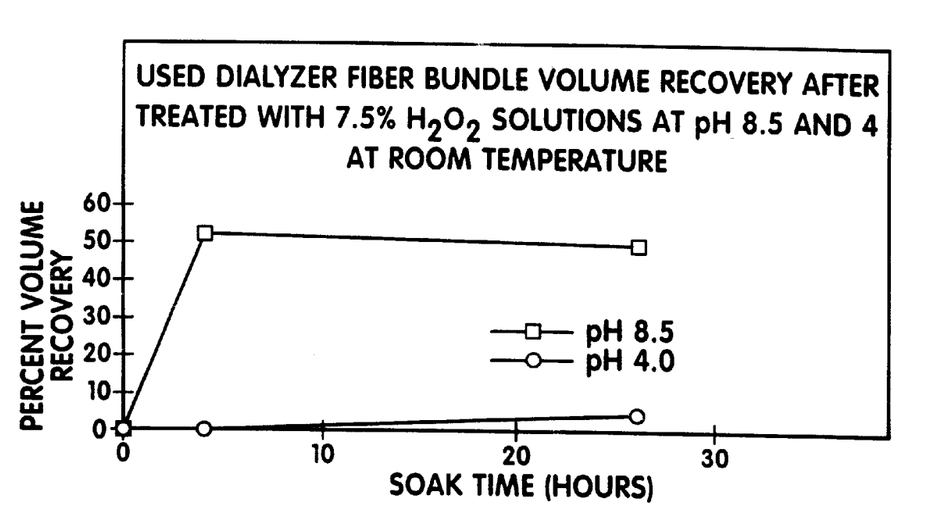
The figure is a graph showing used dialyzer fiber bundle volume recovery after treatment with a solution of the invention.

Both blood and dialysate chambers of the dialyzers were soaked with the above cleaning/disinfecting solutions, one dialyzer per solution, after the water in the dialysate chambers was removed. FIG. 1 shows the relationship between the percentage fiber bundle (blood chamber) volume recovery and the cleaning/disinfecting solution soak time. The percentage fiber bundle volume recovery (P) was determined with the equation:

$$P = 400 \times \text{Fiber Volume Increase}/V_{used}$$

Percentage fiber bundle volume recovery is also=(V Increase/($V_{(new)}$-$V_{(used)}$))×100, wherein $V_{(new)}$ is assumed to be 1.25×$V_{(used)}$. This example shows that the alkaline H$_2$O$_2$ solution can effectively remove the blood proteins clotted in the dialyzer fiber bundles (about 50% recovery of clotted fiber bundle volumes within 4 hours) and that the acidic H$_2$O$_2$ solution has no significant effect on removing the clotted blood protein in the dialyzers. The negative results obtained with the acidic H$_2$O$_2$ solution are consistent with the fact that these used dialyzers had been processed repeatedly from their new state to the end of their useful life with the diluted Renalin® Dialyzer Reprocessing Concentrate from the Renal Systems Division of the Minntech Corporation. Renalin® is an acidic (pH 2.5) solution of about 0.8%$^{w/v}$ hydrogen peroxide (H$_2$O$_2$) and about 0.14%$^{w/v}$ peracetic acid (PAA) when diluted.

The compositions and the methods using the compositions of the present invention in many cases do not need to be neutralized prior to disposal, as do the currently marketed solutions such as Renalin®. The sanitary disposal of used chemical solutions including cleaners, germicides and liquid chemical germicides are regulated by federal, state and local agencies. Sanitary sewer system disposal regulations are developed by the governing Publicly Owned Treatment Works (POTW) in compliance with the Federal Clean Water Act. Disposal requirements can vary with each POTW and cover a wide range of physical and chemical properties including flammability, pH, pollutant control, health hazards, viscosity, etc. Solutions with acid pH values, such as pH 2.5 which occur with Renalin®, meet the classification of a hazardous waste under the Resource, Conservation and Recovery Act (RCRA, 40 C.F.R. §261.22) and hence must be neutralized for routine disposal into a sanitary sewer system.

EXAMPLE 2

Sporicidal Activity of Hydrogen Peroxide (H$_2$O$_2$) Solutions at Various pH Values The Association of Official Analytical Chemists (AOAC) test for Sporicidal Activity of Disinfectants (AOAC Official Methods of Analysis, 15$^{th}$ edition, 1995) was employed to evaluate the sporicidal activity of H$_2$O$_2$ solutions. No organic soil load was used. Clean porcelain penicylinders (outside diameter (O.D.) 8 mm±1, inside diameter (I.D.) 6 mm±1, length mm±1) were sterilized for 2 h at 180° C. Porcelain penicylinder carriers were immersed for 15 min in a 72±4 h old broth culture containing spores of *Bacillus subtilis* (ATCC #19659) in soil extract-nutrient medium at a ratio of 1 carrier per ml broth culture and placed into a glass petri dish matted with two layers of filter paper. The contaminated carriers were transferred in a vacuum desiccator containing CaCl$_2$ and the vacuum was drawn to 69 cm (27 inches) Hg for 20 min. The contaminated carriers were dried in a desiccator for 42 h.

Solutions of 7.5%$^{w/v}$ H$_2$O$_2$ at various pH values were utilized for this test. The solutions were prepared from a 35.1%$^{w/v}$ solution of H$_2$O$_2$ (Aldrich Chemical Company) that was diluted with the required amount of deionized water. The solution at pH 8.5 additionally contained a small concentration (0.04 mg/ml) of protein load for the purpose of simulating the protein deposit, and which did not interfere with sporicidal activity. Deionized water was tested as a negative control.

Test solutions of H$_2$O$_2$ were placed into duplicate test tubes and equilibrated to 20° C. in a water bath for 10 min. Five of the contaminated porcelain penicylinder carriers were placed into each of two tubes containing the individual test solutions. After a defined period of contact, representing the sterilization time, the carriers were individually removed by hook needle to a subculture medium of Fluid Thioglycollate Medium USP. After completion of subcultures, each carrier was re-transferred to a fresh tube of the same subculture medium. Subculture tubes were incubated for 21 days at 37° C.±2° C. After 21 days the tubes were examined for growth as determined by turbidity. Tubes demonstrating growth were subcultured onto agar medium for confirmation of the test organism. Tubes demonstrating no growth of the test organisms were heat shocked for 20 min at 80° C.±1° C. and reincubated for 72 h±4 h at 35° C.–37° C. Tubes without growth following heat shock were considered negative. The results are shown in Table 1.

TABLE 1

Sporicidal activity of 7.5%$^{w/v}$ H$_2$O$_2$ solutions of various pH values at exposure time of 4 h with 10 carriers.

| pH | Number of Positive Carriers |
|---|---|
| 8.5 | 0 positive/10 carriers |
| 7 | 0 positive/10 carriers |
| 5 | 0 positive/10 carriers |
| 3.9 | 0 positive/10 carriers |

As shown in Table 1, there was no change in sporicidal activity with a change in pH of the H$_2$O$_2$ solution at an exposure time of 4 h. This indicated that H$_2$O$_2$ solutions having a higher pH maintain their sporicidal activity without significant loss.

In contrast to these results, it has been reported (J. Applied Bacteriology, 1983, 54, 417–423) that H$_2$O$_2$ at 0.88 m/l (3.0%$^{w/v}$) lost some sporicidal rate of kill activity at pH 8.0 versus at pH 5.0, while remaining sporicidal at both pH 5 and pH 8, killing all *Bacillus subtilis* spores in 6 h at pH 8.0, and in 3 h at pH 5.0. Similarly, the report found that PAA at 0.013 m/l (0.10%$^{w/v}$) lost some sporicidal rate of kill activity at pH 8.0 versus pH 5.0, while remaining sporicidal at both pH 5 and pH 8, killing all *Bacillus subtilis* spores in >6 h at pH 8.0 and in 1 h at pH 5.0. PAA at pH 2.6 exhibited a similar rate of kill at pH 5.0. However, PAA at between 0.13–0.38 m/l (0.99–2.89%$^{w/v}$) did not show a reduction in sporicidal rate of kill activity between pH 8.0 and pH 5.0. Together, these sporicidal activity tests indicate that the compositions of the invention using peracids alone or in combination with $H_2O_2$ can achieve adequate sporicidal activity, well within the 20 h sporicidal kill FDA standard for high-level disinfectants and sterilants.

EXAMPLE 3

Tuberculocidal Effectiveness of Hydrogen Peroxide ($H_2O_2$) Without Peracetic Acid Several hydrogen peroxide solutions were formulated without any additional preservatives or other antimicrobial agents and without surfactants, chelators or organic buffers, as shown in Table 2.

TABLE 2

| Formulation | Ingredients | Concentration | pH (adjusted with HCl) |
|---|---|---|---|
| BS200-156A | *$H_2O_2$ | 6.0 | 8.5 |
|  | $Na_3PO_4$ | 0.5 |  |
| BS200-156B | $H_2O_2$ | 6.0 | 6.3 |
|  | $Na_3PO_4$ | 0.5 |  |
| BS200-156C | $H_2O_2$ | 6.0 | 5.0 |
|  | $Na_3PO_4$ | 0.5 |  |

*FMC Corporation

Their tuberculocidal effectiveness was evaluated with a quantitative tuberculocidal test (suspension test) designed to determine the tuberculocidal effectiveness of a disinfectant/sterilant following the EPA Guidelines for the Quantitative Tuberculocidal Procedure.

The specific test conditions were as follows. Two sterile glass test tubes each containing 18 ml of a particular test formula at 25° C. were each inoculated with 2 ml of a standardized suspension of *Mycobacterium bovis* (ATCC 35743) containing $1.0 \times 10^6$ Colony Forming Units (CFU)/ml. At contact times of 10 min (156B only) and 30 min (156A, B, and C), aliquots of the test suspension were removed and diluted in a neutralizer solution containing catalase to inactivate the $H_2O_2$. Serial tenfold dilutions of the neutralized suspension were then made in sterile saline. Each dilution was filtered through a 47 mm membrane filter with 0.45 micron porosity with the aid of a vacuum. Each filter was removed and aseptically placed on the surface of a Middlebrook 7H11 agar plate. The plates were incubated at 37° C.±2° C. for 15–25 days. Colonies were counted and the average CFU/ml was calculated for each contact time. The $\log_{10}$ reduction was determined by subtracting the survivors at each contact time from the $\log_{10}$ CFU/ml at time zero (to). The results are presented in the following table.

TABLE 3

Tuberculocidal activity test results

| Formulation | pH | 0 min (CFU/ml) | 10 min (CFU/ml) | 30 min (CFU/ml) |
|---|---|---|---|---|
| BS200-156A | 8.5 | $1.0 \times 10^6$ | NA | $3.5 \times 10^5$ |
|  | 8.5 | $1.0 \times 10^6$ | NA | $1.2 \times 10^5$ |
|  |  | Average = $1.0 \times 10^6$ |  | Average = $2.35 \times 10^5$ $\log_{10}$ reduction = 0.63 |
| BS200- | 6.3 | $1.0 \times 10^6$ | $1.0 \times 10^6$ | $1.20 \times 10^5$ |

TABLE 3-continued

Tuberculocidal activity test results

| Formulation | pH | 0 min (CFU/ml) | 10 min (CFU/ml) | 30 min (CFU/ml) |
|---|---|---|---|---|
| 156B | 6.3 | $1.0 \times 10^6$ | $1.1 \times 10^6$ | $1.10 \times 10^6$ |
|  |  | Average = $1.0 \times 10^6$ | Average = $1.05 \times 10^6$ $\log_{10}$ reduction = 0.00 | Average = $6.10 \times 10^5$ $\log_{10}$ reduction = 0.21 |
| BS200-156C | 5.0 | $1.0 \times 10^6$ | NA | $1.1 \times 10^5$ |
|  | 5.0 | $1.0 \times 10^6$ | NA | $1.1 \times 10^5$ |
|  |  | Average = $1.0 \times 10^6$ |  | Average = $1.1 \times 10^5$ $\log_{10}$ reduction = 0.96 |

The results of these tests indicate that $H_2O_2$ solutions alone up to 6–8%$^{w/v}$ or more, without any additional preservative or other antimicrobial agents and without surfactants, chelators or organic buffers, cannot achieve in a short time interval one of the fundamental antimicrobial efficacy requirements for a high-level disinfectant, namely tuberculocidal activity. Example 4 demonstrates tuberculocidal activity in a short time interval.

EXAMPLE 4

Tuberculocidal Tests of Hydrogen Peroxide ($H_2O_2$) plus Peracetic Acid (PAA) Solutions Several $H_2O_2$ plus PAA solutions were formulated and their tuberculocidal effectiveness was evaluated with a quantitative tuberculocidal test (suspension test), as in the previous example.

TABLE 4

Formulations (all concentrations expressed as %$^{w/v}$

| Ingredients | LC203-86A | LC203-86B | LC203-87A | LC203-87B |
|---|---|---|---|---|
| $H_2O_2$ | 5 | 5 | 5 | 5 |
| Peracetic Acid | 0.1 | 0.2 | 0.3 | 0.4 |
| Benzotriazole | 0.65 | 0.65 | 0.65 | 0.65 |
| Dequest | 0.5 | 0.5 | 0.5 | 0.5 |
| Acetic Acid | 0.8 | 0.8 | 0.8 | 0.8 |
| pH | 3 | 3 | 3 | 3 |

TABLE 5

Tuberculocidal activity test results.

| Formulation | 0 min (CFU/ml) | 10 min (CFU/ml) | 20 min (CFU/ml) | 25 min (CFU/ml) |
|---|---|---|---|---|
| LC203-86A | $1.0 \times 10^6$ | 0.0 $\log_{10}$ reduction = 6.0 | 0.0 $\log_{10}$ reduction = 6.0 | 0.0 $\log_{10}$ reduction = 6.0 |

| Formulation | 0 min (CFU/ml) | 10 min (CFU/ml) | 15 min (CFU/ml) | 20 min (CFU/ml) |
|---|---|---|---|---|
| LC203-86B | $1.0 \times 10^6$ | 0.0 $\log_{10}$ reduction = 6.0 | 0.0 $\log_{10}$ reduction = 6.0 | 0.0 $\log_{10}$ reduction = 6.0 |
| LC203-87A | $1.0 \times 10^6$ | 0.0 $\log_{10}$ reduction = 6.0 | 0.0 $\log_{10}$ reduction = 6.0 | 0.0 $\log_{10}$ reduction = 6.0 |

TABLE 5-continued

Tuberculocidal activity test results.

| Formulation | | | | |
|---|---|---|---|---|
| LC203-87B | $1.0 \times 10^6$ | $0.0$ $\log_{10}$ reduction = 6.0 | $0.0$ $\log_{10}$ reduction = 6.0 | $0.0$ $\log_{10}$ reduction = 6.0 |

The results in Table 5 show that all of the solutions representing compositions of the present invention tested at all time intervals exhibited maximum tuberculocidal activity, with a 6 $\log_{10}$ reduction, or total kill, of the entire initial innoculum challenge. Benzotriazole does not contribute to the tuberculocidal activity of the solution. The solution pH 3 is also not considered to be significant, as the work of Baldry and others, together with the above example, indicate that solutions comprising peracetic acid at a higher pH can achieve adequate tuberculocidal activity. Specifically, even the lowest concentration of peracetic acid tested at pH 3 in Table 5, $0.10\%^{w/v}$, achieved a 6 $\log_{10}$ reduction in 10 min. The work of Baldry indicated a factor of 6 times increase in sporicidal kill time for peracetic acid at pH 8.0 versus 5.0, and a possible factor of 2 times increase in kill time at pH 2.6 versus pH 5.0. Overall, the sporicidal activity of peracetic acid as measured by Baldry did not decrease by more than a factor of 3–10 times between pH 2.6 and pH 8.0. In this context, the antimicrobial activity of undissociated peracetic acid is known to exceed that of the anion formed upon dissociation, and the pKa of peracetic acid is 8.2. Thus, the observed changes in antimicrobial activity of peracetic acid are consistent with its pKa. Tuberculocidal activity is expected to exhibit the same pH relationship, given the indiscriminate mode of action of peracetic acid on cells. Therefore, even a 10 times increase in the 10 min tuberculocidal kill time in the example above results in a 100 min required contact time at a higher pH. The total allowed time for high-level disinfection and sterilization, established by FDA guidelines, is a maximum of 20 h. Kidney dialyzers are disinfected and sterilized between dialysis treatments, which are typically every other day and provide a 48 h period between dialysis treatments with which to disinfect and sterilize the dialyzer. Thus the foregoing results and conclusions are reasonable. They are also supported by the known neutral pH sterilization capacity of the $0.2\%^{w/v}$ peracetic acid solution used in the Steris® System1™ Sterile Processing System for endoscope reprocessing (Steris Corp., Mentor, Ohio). This system achieves sterilization at a neutral pH in 12 min at 43–48° C.

EXAMPLE 5

Proteolysis Tests of Hydrogen Peroxide Solutions

Tests were performed to evaluate the proteolytic effects of hydrogen peroxide solutions at various pH values. Azocasein, comprised of the milk protein casein with covalently-bound azo dye molecules linked to amino acid side chains, was exposed to various hydrogen peroxide solutions to determine if the solutions could lyse the casein molecule into small peptide and amino acid fragments, which remain soluble upon exposing the entire solution to trichloracetic acid (TCA). The soluble fragments absorb light at 390 nm due to the presence of the azo dye. Intact azocasein is insoluble in TCA. Therefore, the method can detect proteolysis and provides a quantitative measure of protein removal (e.g., cleaning) capacity. This is also a standard method to detect enzymatic proteolysis.

Azocasein powder was added to $7.5\%^{w/v}$ $H_2O_2$ and 10 mM potassium phosphate buffer ($K_2HPO_4$) or 10 mM potassium phosphate buffer solutions at various pH values (adjusted with 1 N NaOH) to yield an azocasein concentration of $0.4\%^{w/v}$. After 30 min at 23° C., 5 ml of the azocasein solution was mixed with 5 ml of $10\%^{w/v}$ TCA solution. The precipitates of the solutions were removed after 15 min by filtration, and the absorbance of the supernatant was measured at 390 nm ($Abs_{390}$) using a UV-visible spectrophotometer. The absorbance of the azocasein solution ($0.4\%^{w/v}$) containing phosphate buffer alone, without hydrogen peroxide, was measured as a control. While it can be dissolved in all of the above solutions at pH 8 and pH 5 within a few minutes with stirring, azocasein virtually does not dissolve at pH 2. The results are presented in Table 6.

TABLE 6

Absorbance at 30 min contact time of hydrolyzed azocasein solution at 390 nm containing $7.5\%^{w/v}$ $H_2O_2$ and/or potassium phosphate buffer at various pH values at 23° C.

| pH | $7.5\%^{w/v}$ $H_2O_2$/Phosphate Buffer | 10 mM Potassium Phosphate Buffer Control |
|---|---|---|
| 8.0 | 0.0662 | 0.0455 |
| 5.0 | 0.0624 | 0.0481 |
| 2.0 | 0.0536 | 0.0287 |

Although azocasein can be dissolved in the solutions at pH 8 and 5, the absorbance of the solutions as shown in Table 5 remained nearly as low as that of pH 2 solutions. At all pH values, the azocasein hydrolysis rate is higher in $7.5\%^{w/v}$ $H_2O_2$ solutions than in the corresponding phosphate buffer solutions, although not significantly so, indicating the lack of substantial protein hydrolysis/cleaning efficiency.

EXAMPLE 6

Proteolytic Activity in $H_2O_2$ Solutions Over Time

The initial $7.5\%^{w/v}$ $H_2O_2$/potassium phosphate buffer solutions were prepared with standard procedures as in Example 5. One half hour prior to the time points listed in Table 7, azocasein powder was added to aliquots of the solutions in an amount of 0.4% of the total solution weight. The solution absorbance was measured following the same procedures as in Example 5 except the supernatant of the azocasein/TCA solutions was diluted 6–7 fold to avoid saturation of the UV spectrophotometer. The results are presented in Table 7.

TABLE 7

(Dilution Factor) × ($AbS_{390nm}$) of hydrolyzed azocasein solution containing $7.5\%^{w/v}$ $H_2O_2$ and 10 mM potassium phosphate buffer at pH 8.0 and pH 5.0 at 23° C.

| pH | Time (h) | $7.5\%^{w/v}$ $H_2O_2$/10 mM Phosphate Buffer ($AbS_{390nm}$) |
|---|---|---|
| 8.0 | 0.5 | 0.0662 |
| | 2.5 | 0.1644 |
| | 5.5 | 0.2611 |
| | 8 | 0.389 |
| 5.0 | 0.5 | 0.0624 |
| | 2.5 | 0.1238 |
| | 5.5 | 0.2041 |
| | 8 | 0.3145 |

These results show that the cumulative azocasein hydrolysis increased over 8 h to a significant level at both pH conditions, well beyond that of phosphate buffer alone (which produces an absorbance about one half that of the $H_2O_2$-containing solution at pH 8.0, not shown) and that hydrolysis was greater at pH 8.0 than pH 5.0.

EXAMPLE 7

Proteolytic Activity in $H_2O_2$ and PAA Solutions at Various pH Values

Solutions of $1.08\%^{w/v}$ $H_2O_2/0.2\%^{w/v}$ PAA were prepared by diluting a stock of $26.5\%^{w/v}$ $H_2O_2$ and $4.9\%^{w/v}$ PAA (Degussa, density 1.12 g/ml). The pH values were adjusted with 1 N NaOH in the presence of 10 mM $K_2HPO_4$ solution. Azocasein powder was added to the solutions to yield an azocasein concentration of $0.4\%^{w/v}$. After dissolved azocasein stood for 30 minutes at 23° C., 5 ml of the azocasein solution was mixed with 5 ml of 10% TCA solution. The precipitates of the solutions were removed after 15 min by filtration and $Abs_{390}$ of the supernatant was measured using a UV-visible spectrophotometer. The absorbance of an azocasein solution ($0.4\%^{w/w}$) containing phosphate buffer alone, without $H_2O_2$ and PAA, was measured as a control. Additional solutions were prepared containing Alcalase® 2.5 L, a serine-protease enzyme (Novo Nordisk, Copenhagen, Denmark) to serve as positive controls, as it has been discovered that such enzymes exhibit equal or greater activity in these $H_2O_2$/PAA solutions as in phosphate buffer solutions as disclosed in copending U.S. patent application Ser. No. 09/183,186, Simultaneous Cleaning and Disinfecting Compositions and Methods invented by Huth et al. The $H_2O_2$/PAA solutions were mixed with Alcalase® 2.5 L in a volume ratio of 1280:1, yielding a solution with a nominal enzyme activity of 0.0021 Anson units/ml.

TABLE 8

$Abs_{390}$ of hydrolyzed azocasein solution containing $1.08\%^{w/v}$ $H_2O_2$, $0.2\%^{w/v}$ PAA and potassium phosphate versus potassium phosphate alone, with and without Alcalase ® at various pH values at 23° C.

| pH | $1.08\%^{w/v}$ $H_2O_2/0.2\%^{w/v}$ PAA | $1.08\%^{w/v}$ $H_2O_2/0.2\%^{w/v}$ PAA/ Alcalase ® 2.5 L | 10 mM Potassium Phosphate Buffer/Alcalase ® 2.5 L | 10 mM Potassium Phosphate Buffer |
|---|---|---|---|---|
| 8.0 | 0.2566 | 2.135 | 1.783 | 0.0502 |
| 5.0 | 0.3181 | 1.122 | 1.023 | 0.0459 |
| 2.0 | 0.1284 | 0.1244 | 0.0323 | 0.03 |

Comparing absorbance data in Tables 6 and 8, one can see that the mixed solutions of 1.08% $H_2O_2$/0.2% PAA without enzyme can hydrolyze 4–5 times more azocasein than $7.5\%^{w/v}$ $H_2O_2$ solution without enzyme in the same time period at pH 5 and pH 8. Furthermore, although 0.4% azocasein was poorly dissolved in the $H_2O_2$/PAA solutions at pH 2, the partially dissolved azocasein molecules are hydrolyzed about 2 times faster than in the 7.5% $H_2O_2$ solutions, without enzyme. Table 8 shows that the absorbance of hydrolyzed azocasein solutions in the mixed solutions of $H_2O_2$/PAA and enzyme is higher than that in the corresponding phosphate buffer solutions containing enzyme at pH 5 and pH 8 or the corresponding solutions that do not contain enzyme. It is surprising, however, that the $H_2O_2$/PAA solutions that do not contain enzyme produce between 12–14% of the hydrolysis activity of the corresponding $H_2O_2$/PAA enzyme solutions at pH 8.0, and between 28–31% of the hydrolysis activity of the corresponding $H_2O_2$/PAA enzyme solutions at pH 5.0. The pH difference is largely due to the pH activity range for Alcalase® 2.5L, which has an optimal activity range between about pH 6–12, with a peak cleaning activity between about pH 8–8.5.

EXAMPLE 8

Proteolytic Activity in $H_2O_2$/PAA Solutions at pH 5.6 Over Time

A $1.08\%^{w/v}$ $H_2O_2/0.2\%^{w/v}$ PAA solution containing 10 mM potassium phosphate buffer was adjusted to pH 5.6 with 1 N NaOH. The solution was then mixed with azocasein powder to result in $2\%^{w/w}$ azocasein at 23° C. Three ml of the above solution was removed at each time point and was mixed with 3 ml of 10% TCA solution. The precipitates of the solutions were removed after 15 min by filtration, and $Abs_{390}$ of the supernatant was measured using a UV-visible spectrophotometer. Azocasein/TCA solutions were diluted 6–7 fold to avoid saturation of the UV spectrophotometer.

TABLE 9

$Abs_{390}$ of hydrolyzed azocasein solution containing $1.08\%^{w/v}$ $H_2O_2/2.0\%$ PAA and 10 mM $K_2HPO_4$ at pH 5.6 at 23° C.

| Time (h) | 1.08% $H_2O_2$/0.2% PAA/10 mM $K_2HPO_4$ |
|---|---|
| 0.5 | 0.937 |
| 3.0 | 1.46 |

The results show that substantial hydrolysis of azocasein occurs in this system at both time intervals. Since the azocasein concentration was five times that in the preceding Example 7 (i.e., 2% versus 0.4%), this difference in protein substrate (azocasein) concentration possibly accounts for the large difference in results seen at 30 min (e.g., $Abs_{390}$ 0.937 in this example versus $Abs_{390}$ 0.3181 in Example 7 at 30 min).

Example 1 shows that $7.5\%^{w/v}$ $H_2O_2$ at pH 8.5 can restore about 50% of clotted dialyzer fiber bundle volume in 4 h. However, Example 3 shows that $6.0\%^{w/v}$ $H_2O_2$ at pH 5.0–8.5 is not tuberculocidal between 10–30 min. Moreover, the data indicate that a 6.0 $\log_{10}$ reduction, the standard for tuberculocidal activity for a high-level disinfectant within the regimen soak time, would not be achieved by a $6.0\%^{w/v}$ or even $7.5\%^{w/v}$ $H_2O_2$ solution in under about 5 h, since only a 0.63 $\log_{10}$ reduction was achieved in 30 min by the $6.0\%^{w/v}$ $H_2O_2$ solution. Examples 4–8 show that mixtures of $H_2O_2$ and PAA can achieve high-level disinfection standards and 4–5 times greater hydrolysis of protein than $7.5\%^{w/v}$ $H_2O_2$ alone. This indicates that such solutions can achieve greater restoration of clotted kidney dialyzer fiber bundle volume than that observed with the $7.5\%^{w/v}$ $H_2O_2$ solution and also adequately disinfect and sterilize dialyzers in a reasonable time frame.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed is:

1. A composition for cleaning and decontaminating a dialyzer comprising (a) a source of at least one per-compound oxidant and (b) a buffer in amounts to provide said per-compound oxidant at a concentration and pH effective for cleaning and decontaminating.

2. The composition of claim 1 wherein said pH is between about pH 5 and pH 11.

3. The composition of claim 1 wherein said per-compound oxidant is selected from the group consisting of at least one peracid and hydrogen peroxide ($H_2O_2$) and at least one peracid.

4. The composition of claim 3 wherein said $H_2O_2$ is at a concentration in the range of about $1–50\%^{w/v}$.

5. The composition of claim 3 wherein said $H_2O_2$ is at a concentration in the range of about $3–20\%^{w/v}$.

6. The composition of claim 3 wherein said $H_2O_2$ is at a concentration in the range of about $6.5–8\%^{w/v}$.

7. The composition of claim 3 wherein said peracid is at a concentration in the range of about $0.0050–10.0\%^{w/v}$.

8. The composition of claim 1 wherein said per-compound oxidant is a mixture of peracetic acid at about $0.0050–0.5\%^{w/v}$ and $H_2O_2$ at about $0.5–50.0\%^{w/v}$.

9. The composition of claim 1 wherein said per-compound oxidant is a mixture of peracetic acid at about $0.005–0.2\%^{w/v}$ and $H_2O_2$ at about $0.5–8.0\%^{w/v}$.

10. The composition of claim 1 wherein said buffer is selected from the group consisting of acetic acid, propanoic acid, glycine, monobasic dihydrogen phosphate, dibasic hydrogen phosphate, bicarbonate, carbonate, and combinations thereof.

11. The composition of claim 10 wherein said buffer contains non-immunogenic counter ions.

12. A method of cleaning and decontaminating a dialyzer comprising (a) producing a solution by combining at least one per-compound oxidant and a buffer in amounts to provide said per-compound oxidant at a concentration and pH effective for cleaning and decontaminating wherein said oxidant and said buffer are mixed prior to use, and (b) contacting said dialyzer with said solution for a period of time effective for cleaning and decontaminating.

13. The method of claim 12 further comprising a step (c) of removing said solution from said dialyzer following step (b).

14. The method of claim 13 wherein said removing in step (c) is by rinsing with a liquid selected from the group consisting of sterile water and sterile saline.

15. The method of claim 14 wherein said removing in step (c) is followed by storing said dialyzer to prevent recontamination.

16. The method of claim 14 further comprising removing soil from said dialyzer before step (b).

17. The method of claim 16 wherein said soil removing comprises contacting said dialyzer with a solution comprising an enzyme.

18. The method of claim 14 wherein said removing in step (c) is followed by storing said dialyzer to prevent recontamination.

19. The method of claim 12 wherein said buffer is selected from the group consisting of acetic acid, propanoic acid, glycine, monobasic dihydrogen phosphate, dibasic hydrogen phosphate, bicarbonate, carbonate, and combinations thereof.

20. The method of claim 19 wherein said buffer contains non-immunogenic counter ions.

21. The method of claim 12 wherein said per-compound oxidant is selected from the group consisting of at least one peracid and hydrogen peroxide ($H_2O_2$) and at least one peracid.

22. A method of cleaning and decontaminating a dialyzer having a blood chamber and a dialysate chamber comprising combining at least one per-compound and a buffer in amounts and at a pH effective to form a cleaning and decontaminating solution, and contacting at least said blood chamber with said solution for a time effective for cleaning and decontaminating.

23. The method of claim 22 further comprising venting said dialyzer for escape of a gas formed from said per-compound.

24. The method of claim 22 further comprising contacting said dialysate chamber with said solution.

25. The method of claim 22 wherein said per-compound oxidant is selected from the group consisting of at least one peracid and hydrogen peroxide ($H_2O_2$) and at least one peracid.

26. The method of claim 22 wherein said blood chamber contains fiber bundles having two ends and said contacting is by filling said fiber bundles with said solution, thereafter capping one of said ends with a gas- and solution-impermeable cap and capping the other of said ends with a gas-venting cap.

27. A method for cleaning and high level disinfecting a dialyzer comprising (a) producing a solution by combining at least one per compound oxidant and a buffer in amounts to provide said per-compound oxidant at a concentration and pH effective for cleaning and high level disinfecting wherein said oxidant and said buffer are mixed prior to use, and (b) contacting said dialyzer with said solution for a period of time effective for cleaning and high level disinfecting.

28. A method for cleaning and sterilizing a dialyzer comprising (a) producing a solution by combining at least one per compound oxidant and a buffer in amounts to provide said per-compound oxidant at a concentration and pH effective for cleaning and sterilizing wherein said oxidant and said buffer are mixed prior to use, and (b) contacting said dialyzer with said solution for a period of time effective for cleaning and sterilizing.

29. A composition for cleaning and decontaminating a dialyzer consisting essentially of (a) a source of at least one per-compound oxidant and (b) a buffer in amounts to provide said per-compound oxidant at a concentration and pH effective for cleaning and decontaminating.

* * * * *

UNITED STATES PATENT AND TRADEMARK OFFICE
CERTIFICATE OF CORRECTION

PATENT NO. : 6,468,472 B1  Page 1 of 1
DATED : October 22, 2002
INVENTOR(S) : Yu et al.

It is certified that error appears in the above-identified patent and that said Letters Patent is hereby corrected as shown below:

Title page,
Item [56], OTHER PUBLICATIONS, "Martin et al." reference, reads "Preventoin" and should read -- Prevention --.
Murthy et al." reference, reads "High-Flus" and should read -- High-Flux --.

Column 3,
Line 19, reads "Nephrol:464472" and should read -- Nephrol:464-472 --.

Column 7,
Line 48, reads "50.0%-, are used" and should read -- 50.0%$^{w/v}$, are used --.

Column 12,
Line 17, reads "35.1%$^{w/v}$" and should read -- 35.1%$^{w/w}$ --.

Column 17,
Line 11, reads "26.5%$^{w/v}$...4.9%$^{w/v}$" and should read -- 26.5%$^{w/w}$...4.9%$^{w/w}$ --.

Signed and Sealed this

Fifteenth Day of July, 2003

JAMES E. ROGAN
*Director of the United States Patent and Trademark Office*